(12) United States Patent
Horton et al.

(10) Patent No.: US 10,603,153 B2
(45) Date of Patent: *Mar. 31, 2020

(54) HERNIA PATCH

(71) Applicant: ATRIUM MEDICAL CORPORATION, Merrimack, NH (US)

(72) Inventors: Anthony R Horton, Bedford, NH (US); Paul Martakos, Pelham, NH (US); Steve A Herweck, Wellesley, MA (US); Theodore Karwoski, Hollis, NH (US); Joseph F Ferraro, Londonderry, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/948,844

(22) Filed: Nov. 23, 2015

(65) Prior Publication Data
US 2016/0074148 A1   Mar. 17, 2016

Related U.S. Application Data

(63) Continuation of application No. 13/782,779, filed on Mar. 1, 2013, which is a continuation of application
(Continued)

(51) Int. Cl.
*A61F 2/00* (2006.01)
*A61L 31/10* (2006.01)
(Continued)

(52) U.S. Cl.
CPC ............ *A61F 2/0063* (2013.01); *A61L 31/10* (2013.01); *A61L 31/14* (2013.01); *A61L 31/148* (2013.01);
(Continued)

(58) Field of Classification Search
CPC ............ A61F 2/0063; A61F 2210/0004; A61F 2210/0076; A61F 2220/0008;
(Continued)

(56) References Cited

U.S. PATENT DOCUMENTS

| 1,920,808 A | 8/1933 | Sander |
| 2,499,414 A | 3/1950 | Rabell |

(Continued)

FOREIGN PATENT DOCUMENTS

| EP | 0544485 | 6/1993 |
| EP | 0655222 | 6/1998 |

(Continued)

OTHER PUBLICATIONS https://www.dictionary.com/browse/adjacent; definition for "adjacent" dated Jun. 4, 2019.*

(Continued)

*Primary Examiner* — Jing Rui Ou
(74) *Attorney, Agent, or Firm* — Kevin T. Godlewski; Wesley Scott Ashton

(57) ABSTRACT

A hernia patch supporting tissue in-growth conforms to a tissue wall upon surgical installation and fixation within a patient. The hernia patch can include a base and positioning straps. The base is formed of two layers that are affixed to each other around the perimeter of the patch, for example by stitching. A stabilizing washer is provided between the two layers, and the stitch is provided peripherally around the stabilizing washer, keeping the washer free-floating between the layers. The base, positioning straps, and stabilizing washer are formed of a structure that does not separate the layers of the implant or form a space in the form of a pocket, and promotes more uniform and confluent tissue incorporation or in-growth after implantation. The hernia patch may further include a hydrolysable bioabsorbable cross-linked
(Continued)

coating of a fatty acid based material, such as an omega-3 fatty acid based material.

12 Claims, 8 Drawing Sheets

Related U.S. Application Data

No. 12/877,919, filed on Sep. 8, 2010, now abandoned.

(60) Provisional application No. 61/240,563, filed on Sep. 8, 2009.

(51) Int. Cl.
*A61L 31/14* (2006.01)
*A61K 31/20* (2006.01)

(52) U.S. Cl.
CPC .......... *A61F 2210/0004* (2013.01); *A61F 2210/0076* (2013.01); *A61F 2220/0008* (2013.01); *A61F 2220/0075* (2013.01); *A61F 2230/0004* (2013.01); *A61F 2250/0018* (2013.01); *A61F 2310/00389* (2013.01); *A61K 31/20* (2013.01)

(58) Field of Classification Search
CPC ...... A61F 2220/0075; A61F 2230/0004; A61F 2250/0018; A61F 2310/00389; A61L 31/10; A61L 31/14; A61L 31/148; A61K 31/20
See application file for complete search history.

(56) References Cited

U.S. PATENT DOCUMENTS

| | | | |
|---|---|---|---|
| 3,328,259 A | 6/1967 | Anderson |
| 3,789,828 A | 2/1974 | Schulte |
| 4,271,827 A | 6/1981 | Angelchik |
| 4,271,828 A | 6/1981 | Angelchik |
| 4,769,038 A | 9/1988 | Bendavid et al. |
| 5,086,763 A | 2/1992 | Hathman |
| 5,147,374 A | 9/1992 | Fernandez |
| 5,171,259 A | 12/1992 | Inoue |
| 5,464,403 A | 11/1995 | Kieturkais et al. |
| 5,480,436 A | 1/1996 | Bakker et al. |
| 5,540,711 A | 7/1996 | Kieturkais et al. |
| 5,593,441 A | 1/1997 | Lichtenstein et al. |
| 5,607,443 A | 3/1997 | Kieturkais et al. |
| 5,634,931 A | 6/1997 | Kugel |
| 5,702,416 A | 12/1997 | Kieturkais et al. |
| 5,730,756 A | 3/1998 | Kieturkais et al. |
| 5,766,246 A | 6/1998 | Mulhauser et al. |
| 5,772,680 A | 6/1998 | Kieturkais et al. |
| 5,827,325 A | 10/1998 | Landgrebe et al. |
| 5,836,961 A | 11/1998 | Kieturkais et al. |
| 5,855,613 A | 1/1999 | Antanavich et al. |
| 6,066,776 A | 5/2000 | Goodwin et al. |
| 6,120,539 A | 9/2000 | Eldridge et al. |
| 6,165,225 A | 12/2000 | Antanavich et al. |
| 6,176,863 B1 | 1/2001 | Kugel et al. |
| 6,180,848 B1 | 1/2001 | Flament et al. |
| 6,210,439 B1 | 4/2001 | Firmin et al. |
| 6,258,124 B1 | 7/2001 | Darois et al. |
| 6,264,604 B1 | 7/2001 | Kieturkais et al. |
| 6,312,442 B1 | 11/2001 | Kieturkais et al. |
| 6,342,064 B1 | 1/2002 | Koike et al. |
| 6,350,285 B2 | 2/2002 | Gerlach et al. |
| 6,364,892 B1 | 4/2002 | Jervis |
| 6,372,244 B1 | 4/2002 | Antanavich et al. |
| 6,391,060 B1 | 5/2002 | Ory et al. |
| 6,470,883 B1 | 10/2002 | Beaudry |
| 6,540,764 B1 | 4/2003 | Kieturkais et al. |
| 6,548,081 B2 | 4/2003 | Sadozai et al. |
| 6,570,051 B1 | 5/2003 | Beaudry |
| 6,565,580 B1 | 6/2003 | Beretta |
| 6,592,602 B1 | 7/2003 | Peartree et al. |
| 6,596,002 B2 | 7/2003 | Therin et al. |
| 6,632,234 B2 | 10/2003 | Kieturkais et al. |
| 6,638,312 B2 | 10/2003 | Plouhar et al. |
| 6,695,856 B2 | 2/2004 | Kieturkais et al. |
| 6,790,213 B2 | 9/2004 | Cherok et al. |
| 6,800,082 B2 | 10/2004 | Rousseau |
| 6,982,359 B1 | 1/2006 | Beaudry |
| 7,001,405 B2 | 2/2006 | Kieturkais et al. |
| 7,022,891 B2 | 4/2006 | Beaudry |
| 7,067,710 B1 | 6/2006 | Beaudry |
| 7,101,381 B2 | 9/2006 | Ford et al. |
| 7,160,333 B2 | 1/2007 | Plouhar et al. |
| 7,297,153 B2 | 1/2007 | Kieturakis et al. |
| 7,214,236 B2 | 5/2007 | Kieturakis et al. |
| 7,404,819 B1 | 7/2008 | Darios et al. |
| 7,456,332 B2 | 11/2008 | Beaudry |
| 7,695,487 B2 | 4/2010 | Peartree et al. |
| 7,785,334 B2 | 8/2010 | Ford et al. |
| 7,799,089 B2 | 9/2010 | Plouhar et al. |
| 7,806,905 B2 | 10/2010 | Ford et al. |
| 9,220,585 B2 * | 12/2015 | Horton ................ A61F 2/0063 |
| 2002/0077652 A1 | 6/2002 | Kieturakis et al. |
| 2002/0103494 A1 | 8/2002 | Pacey |
| 2003/0078602 A1* | 4/2003 | Rousseau .............. A61F 2/0063 |
| | | | 606/151 |
| 2004/0039246 A1 | 2/2004 | Gellman et al. |
| 2004/0087980 A1* | 5/2004 | Ford .................. A61B 17/0057 |
| | | | 606/151 |
| 2004/0215219 A1 | 10/2004 | Eldridge et al. |
| 2005/0085924 A1* | 4/2005 | Darois .................. A61F 2/0063 |
| | | | 623/23.74 |
| 2005/0124926 A1 | 6/2005 | Beaudry |
| 2006/0121081 A1 | 6/2006 | Labrecque et al. |
| 2006/0282105 A1 | 12/2006 | Ford et al. |
| 2007/0179512 A1 | 8/2007 | Olsen et al. |
| 2008/0109017 A1 | 5/2008 | Herweck et al. |
| 2008/0172071 A1 | 7/2008 | Barker |
| 2008/0269896 A1* | 10/2008 | Cherok ................ A61F 2/0063 |
| | | | 623/14.13 |
| 2009/0082792 A1 | 3/2009 | Koyfman et al. |
| 2009/0105731 A1 | 4/2009 | Priewe et al. |
| 2009/0171377 A1 | 7/2009 | Intoccia et al. |
| 2009/0181937 A1 | 7/2009 | Faucher et al. |
| 2011/0144667 A1 | 6/2011 | Horton et al. |

FOREIGN PATENT DOCUMENTS

| | | |
|---|---|---|
| EP | 1219265 | 1/2003 |
| EP | 1306061 A2 | 5/2003 |
| WO | WO 1993/10714 | 6/1993 |
| WO | WO 1999/56664 | 11/1999 |
| WO | WO 2002/22047 | 3/2002 |
| WO | WO 2003/073960 | 2/2003 |
| WO | WO 2003/105727 | 12/2003 |
| WO | 2004/012627 A1 | 2/2004 |
| WO | 2004/071349 A2 | 8/2004 |
| WO | 2008/055028 A1 | 5/2008 |

OTHER PUBLICATIONS

Extended European Search Report issued for EP Patent Application No. 10816037.5, dated Jun. 30, 2015, 8 pages.
Bard Ventralex Hernia Patch Technique Guide, 2007.
Bard FDA 510K Approval (Jan. 2001).
Bard Internet Publication (Apr. 2001).
Bellon, et al., "Evaluation of a New Composite Prosthesis (PL-PU99) for the Repair of Abdominal Wall Defects in Terms of Behavior at the Peritoneal Interface," *World Journal of Surgery*, 26: 661-666 (2002).
Bendavid, et al., "A Femoral 'Umbrella' for Femoral Hernial Repair Surgery," *Gynecology and Obstetrics*, 165: 153-156 (1987).
Bendavid, et al., New Techniques in Hernia Repair, *World Journal of Surgery*, 13: 522-531 (1989).

(56) References Cited

OTHER PUBLICATIONS

Greenawalt, et al., "Evaluation of Sepramesh Biosurgical Composite in a Rabbit Hernia Repair Model," *Journal of Surgical Research*, 94: 92-98 (2000).
Helfrich, et al., "Abdominal Wall Hernia Repair: Use of the Gianturco-Helfrich-Eberbach Hernia Mesh," *Journal of Laparoendoscopic Surgery*, 5(2): 91-96 (1995).
Kugel, et al., "Minimally Invasive, Nonlaparoscopic, Preperitoneal, and Sutureless, Inguinal Herniorraphy," *The American Journal of Surgery*, 178: 298-302 (1999).
Lichtenstein, et al., "Repair of Recurrent Ventral Hernias by an internal 'Binder'", *The American Journal of Surgery*, 132: 121-125 (1976).
Moreno-Egea, "Laparoscopic repair of Ventral and Incisional Hernias Using a new Composite Mesh (Parietex)," *Surgical Laparoscopy, Endoscopy & Percutaneous Techniques*, 11(2): 103-106 (2001).
Bard FDA 510K Approval (Jul. 2002).
International Search Report for International Application PCT/US2010/048167, dated Oct. 20, 2010.
Non-Final Office Action for U.S. Appl. No. 12/877,919 (listed on SB-08 as US 2011/0144667,), dated Jun. 6, 2012.
Final Office Action for U.S. Appl. No. 12/877,919 (listed on SB-08 as US 2011/0144667,), dated Nov. 21, 2012.
Non-Final Office Action issued in U.S. Appl. No. 15/817,018, dated Sep. 19, 2018.
Office Action issued in counterpart EP Application No. 10816037.5, dated Jan. 2, 2020, 4 pages.
Written Opinion issued in International Application No. PCT/US2010/048167, dated Oct. 20, 2010, 4 pages.
International Preliminary Report on Patentability issued in International Application No. PCT/US2010/048167, dated Mar. 22, 2012, 6 pages.
Non-Final Office Action issued in U.S. Appl. No. 13/782,779, dated May 21, 2014, 16 pages.
Final Office Action issued in U.S. Appl. No. 13/782,779 dated Jan. 12, 2015, 19 pages.
Office Action issued in EP Application No. 10816037.5 dated Nov. 27, 2017, 5 pages.

\* cited by examiner

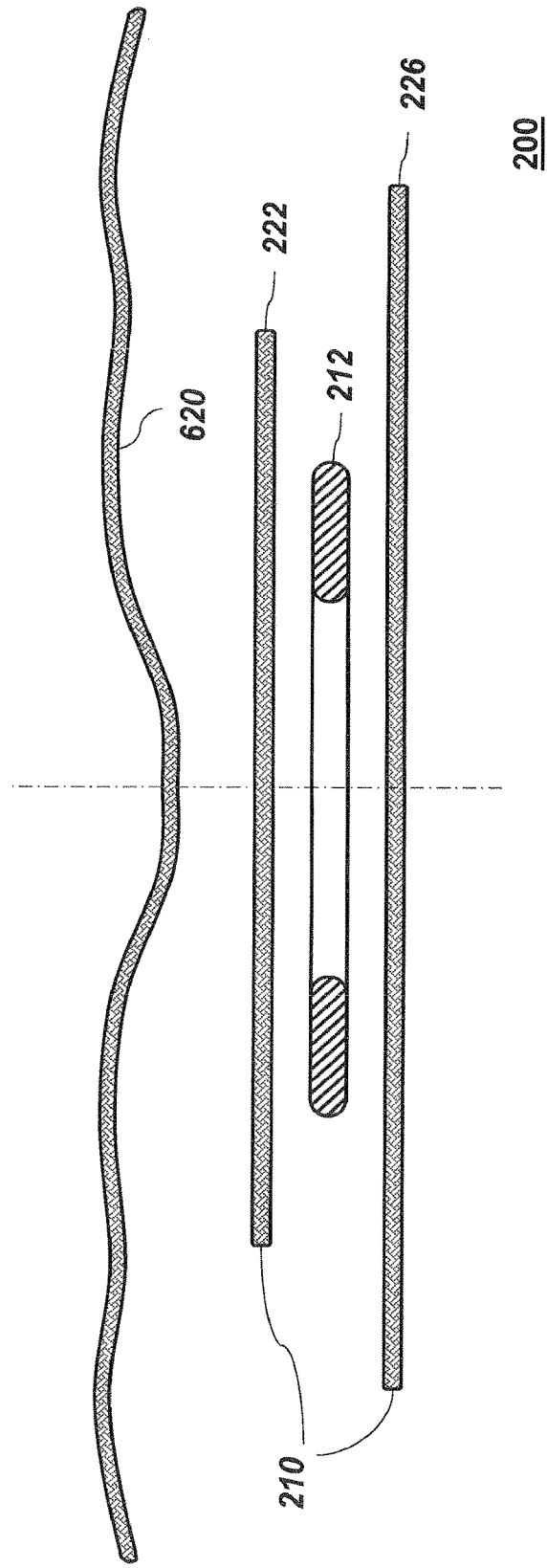
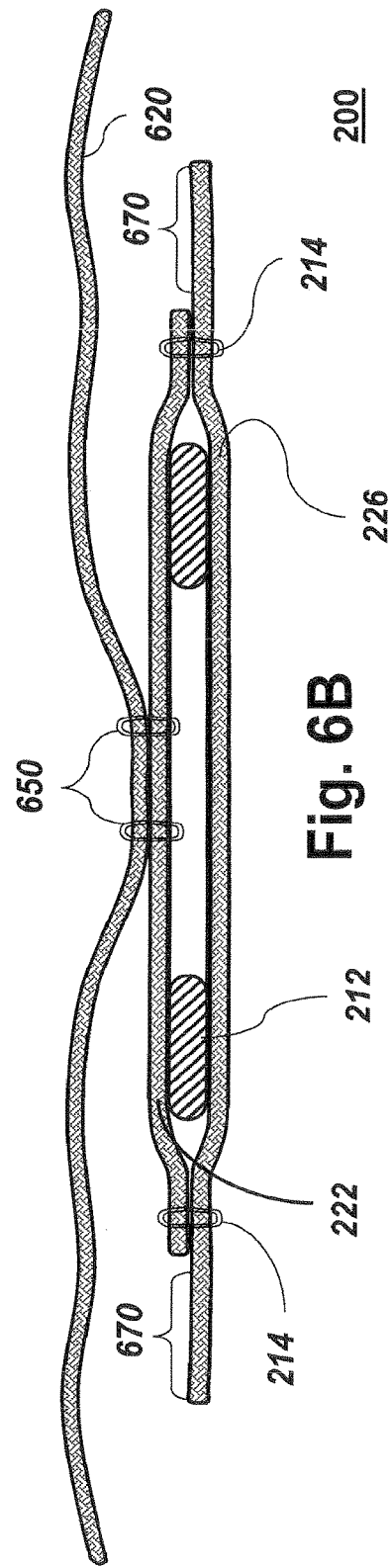

HERNIA PATCH

RELATED APPLICATION

This application is a continuation of, and claims the benefit of, U.S. patent application Ser. No. 13/782,779 (now U.S. Pat. No. 9,220,585 B2), filed Mar. 1, 2013, which is a continuation of U.S. patent application Ser. No. 12/877,919 (now abandoned), filed Sep. 8, 2010, which claims priority to, and the benefit of, U.S. Provisional Application No. 61/240,563, filed Sep. 8, 2009. The entire disclosures of the above applications are incorporated by reference herein.

FIELD OF THE INVENTION

The present invention relates to a device suitable for use in various forms of hernia repair, and more particularly to an implantable hernia patch with improved handling, placement, and implant performance, having a structure that promotes tissue in-growth following implantation into a patient.

BACKGROUND OF THE INVENTION

A hernia is a protrusion of a tissue, structure, or part of an organ through the muscle tissue or the membrane by which it is normally contained. Abdominal hernias are one common type of hernia. In an abdominal hernia, a weakness in the abdominal wall grows into a hole, or defect. Tissue may protrude from the defect. Example hernias include umbilical hernias, in which intra-abdominal contents protrude through a weakness at the site of passage of the umbilical cord through the abdominal wall, and incisional hernias, which occur in an area of weakness caused by an incompletely-healed surgical wound. Those of ordinary skill in the art will appreciate that there are other types of hernias in addition to those specifically mentioned herein.

In order to treat a hernia, such as an umbilical or incisional hernia, a doctor may insert a specially designed patch into an incision near the defect. Such a patch is typically designed to be larger than the defect to ensure adequate coverage. The patch is folded or pushed through the incision. In order to allow the patch to be positioned a hernia patch may include positioning straps, which the doctor pulls on to flatten the patch once it is inside the abdominal wall. The patch is maneuvered into a flat position and moved into a suitable position, as described in more detail below. After the doctor is satisfied with the placement of the patch, the patch may be secured by suturing the positioning straps to the margins of the defect, or by suturing a part of the body of the patch to the connective tissue. Any excess material on the positioning strap is then removed and the incision is closed.

One conventional type of hernia patch is made up of a round base for the patch formed from a number of layers. For example, FIG. 1A and FIG. 1B depict an example conventional hernia patch 100. An example alternative hernia patch is made by, e.g., C.R. Bard, Inc. Warwick, R.I., such as the Ventralex™ hernia patch. As shown in FIG. 1A and FIG. 1B, the base of the hernia patch 100 may be composed of three permanent polymer base layers 105; 110, 120. One of the base layers 120 may be made of low porosity expanded polytetrafluoroethylene (ePTFE) film material, and the second and third base layers 105, 110 may be a polypropylene filament knitted mesh. The smooth ePTFE polymer film layer 120 is intended to act as a non-porous tissue separating layer for blocking and preventing visceral organs from coming into direct physical contact with the polypropylene polymer filament mesh layers 105, 110. The second and third base layers 105, 110 can be formed of a single piece of material, folded over to create the two layers as described below.

One shortcoming of the polymeric-only materials used in some conventional hernia patches is that they may fracture, crack, break, and/or separate when subjected to bending, either during surgical installation, handling, insertion, and fixation, or experience the same mechanical failure after a period of time following insertion due to abdominal wall tension, flexion, compression, and/or stretching. When such common polymer hernia repair materials begin to experience material failure due to mechanical manipulation and disruption, material separation of these components can lead to the formation of sharp edges, which can abrade, irritate, and/or perforate adjacent organ tissue in and around the vicinity of the hernia repair.

In the conventional hernia patch 100, a perimeter 122 of the base is composed of a layer of densified polypropylene bonded to a layer of ePTFE film to create the ePTFE polymer film layer 120. As a result, the perimeter 122 has a high degree of radial and planar stiffness, with a relatively high material density (e.g., when composed of a solid polymer).

As utilized herein, the term "stiffness" is intended to have its conventional definition of a measurement of the resistance of an elastic body to deformation when a force is applied along a given degree of freedom. Likewise, as utilized herein, the terms "flexibility" and "elasticity" relate to the ability of a material to elastically deform when a force is applied along a given degree of freedom, but not plastically deform. A material or structure is considered to be flexible as utilized herein when the material or structure deforms with application of force, but when the force is removed, the material returns to its original shape prior to the application of force, without the requirement of heat. That is, the flexible or elastic material is not a shape memory material, which can return to its cold forged shape but only after application of heat.

This relative stiffness of the conventional hernia patch 100 means that the conventional hernia patch 100 takes its own shape and does not conform itself well to the contours of tissue, such as a patient's abdominal wall. While it does have some flexibility, such that it can be folded in half during implantation and then it will return to its original shape once the force is removed, it does not have a sufficiently high relative amount of flexibility or elasticity to respond well to the much smaller forces applied to the patch 100 as it is pressed up against a tissue wall. Further, because the densified perimeter 122 polymer structure does not possess or exhibit a sufficient macro porosity for tissue in-growth, thereby permanently limiting the material from becoming incorporated by remodeling tissue involved in healing at the implant site, these non-conforming structures often become at risk for mechanical disruption, material contraction, and/or device protrusion into other surrounding tissues following implantation. This lesser degree of tissue in-growth or cellular incorporation often leads to material encapsulation involving chronic inflammation and stimulation of dense, a-cellular connective tissue implicated in visceral organ adhesion formation between the non-porous polymer portion of the patch and the abdominal wall. Such undesirable non-healing effects have further been implicated in published reports of higher reoccurrence rates of the primary hernia repair, chronic pain, and subsequent reintervention requirements to surgically repair the post operative complication.

In the example conventional hernia patch 100, some of its high degree of stiffness results from the existence of a monofilament polymeric stiffening ring 130 that is attached, or stitched into the periphery of the base between the two base layers 105, 110, inside of a pocket 150 formed therebetween. The stiffening ring 130 is sewed or permanently locked into position between the two mesh layers 105, 110. The stiffening ring 130 may be a memory material that memorizes a shape and returns to the memorized shape after being subjected to deformation. This may allow the conventional hernia patch 100 to unfold or open immediately following folded insertion through an incision. For example, in one type of hernia patch, the stiffening ring is made of either an extruded monofilament or molded polyethylene terephthalate (PET) ring that is stitched into the periphery of the mesh base between the two polypropylene mesh layers (105 and 110). The stiffening ring 130 is held in tight proximity to the base materials by peripheral stitching. Alternatively, the stiffening ring 130 may be embedded in one of the base layers.

In the conventional hernia patch 100, positioning straps 140 are attached to the above-described layers of mesh to facilitate placement and fixation. The positioning straps 140 transition from the polypropylene base layer 110, and the positioning straps 140 are a continuation of the same piece of mesh as the polypropylene base layer 110.

In the example conventional hernia patch 100, a slit exists in the polypropylene mesh layer 110 between the two positioning straps 140. This slit provides an opening into a pocket 150 between the polypropylene mesh layers 105, 110. When the positioning straps 140 are placed under tension, such as by pulling the straps 140 apart, the slit opens and the pocket 150 becomes accessible. A doctor may use the pocket 150 with either a finger or instrument to further deploy, flatten out, or to position the conventional hernia patch 100 once the conventional hernia patch 100 is inserted into the incision.

The conventional hernia patch 100 is stitched in two locations. An interior stitching 160 is provided in an interior part of the patch, located between the point where the straps 140 transition into the polypropylene base layer 110 and the stiffening ring 130, but still close or proximal to the stiffening ring. This interior stitching penetrates through all three base layers 105, 110, 120. An outer stitching 170 is provided between the stiffening ring and the periphery of the conventional hernia patch 100. This peripheral stitching penetrates through the two polypropylene mesh base layers 105, 110, but not the ePTFE base layer 120.

Due to the above-described configuration of the stiffening ring 130, positioning straps 140, pocket 150, and stitching 160, 170 in the conventional hernia patch 100, the above-described shortcomings regarding positioning the patch 100 and conforming the patch to the contours of the patient's abdominal wall may exist. Because the stiffening ring 130 is fixed to the base layers 105, 110, 120 via the interior stitching 160, the straps 140 transition into the polypropylene base layer 110, and a slit exists in the polypropylene base layer 110 between the straps 140, when tension is applied by the straps as they are pulled up and out through the hernia defect for suture fixation outside of the abdominal cavity, but within the incision of the abdominal wall, the center of the conventional hernia patch 100 pulls up into the hernia defect while the perimeter of the conventional hernia patch 100 tends to separate away from the tissue wall adjacent to the hernia defect with which it is meant to be in direct contact. This creates a large open space between the polypropylene base layers 110 and 105 that can delay tissue in-growth and healing. When this required tension is applied to these straps for device positioning and fixation, it causes significant separation of the material layers and formation of the pocket 150. The indwelling intra-abdominal cavity portion of the base layer material of the conventional hernia patch 100 tends to yield to the tension applied by the positioning and fixation straps by stretching upward, lifting and bending away from the abdominal wall. This creates a non-uniform and/or irregular shaped surface profile that is often a substantially conical shape in appearance, leaving an undesirable gap or open space between the perimeter body of the conventional hernia patch 100 and the abdominal wall. This space becomes difficult for tissue to heal across, thereby requiring greater lengths of time for connective tissue to fill in between the perimeter rim of the patch. Such spaces can further lead to complications of visceral organ entrapment involved with adhesion formation.

In a 28-day swine preclinical study, the limitations of a conventional hernia patch were confirmed. A conventional hernia patch was implanted into midline hernia detects of a swine test subject, and laparoscopic images were taken at days 1, 7, 14, and 28 post-implantation. At 28 days, the patch was explanted and gross explant photographs were taken.

Images of the conventional hernia patch (see FIG. 7B) show that after 24 hours in-vivo, a space was formed between the perimeter of the conventional hernia patch and the tissue above the patch. Cross sectional photographs taken at explant 28 days after implantation (see FIG. 8B), large spaces continued to exist between the perimeter of the conventional patch and the abdominal wall.

SUMMARY

There is a need for a hernia patch constructed of a structural material that mechanically contours uniformly along the plane of the tissue involved in surgical repair of a hernia (e.g., abdominal wall) during installation and strap fixation, and promotes uniform tissue incorporation and in-growth without material layer separation and/or pocket formation. The present invention is directed toward further solutions to address this need, in addition to having other desirable characteristics.

In accordance with one exemplary embodiment, a hernia patch is provided that includes a base and positioning straps. In accordance with one exemplary embodiment, the base is formed of two layers that are attached to each other substantially along their perimeters, for example by stitching. A stabilizing washer is provided in a compartment formed between the two layers, and the stitching is disposed peripheral to the stabilizing washer. The stabilizing washer is not fixed to the base layers, but rather is independent of the base layers, and therefore free-floating within the compartment. Positioning straps are attached to the base, for example by stitching the positioning straps to a top layer of the base at a central position. The positioning straps can be used to position the patch during a hernia repair.

In one exemplary embodiment, the stabilizing washer is constructed of three layers of coated mesh. The mesh may be coated with a fatty acid based material, including a hydrolysable bioabsorbable cross-linked fatty acid based material. In some embodiments, the washer is coated with a fish oil, such as an omega-3 fatty acid (O3FA).

In accordance with one exemplary embodiment of the present invention, a patch for treating a hernia includes a base having two layers and a tissue conformable stabilizing washer disposed in a compartment between the two layers, wherein the two layers are affixed to each other at a location between an outer periphery of the stabilizing washer and an outer periphery of the base. A positioning strap can be attached to the base in such a way that when a pull force is applied thereto such as during implantation the two layers of the base are not substantially pulled apart from each other and the base remains substantially flat and tissue conformable.

In accordance with aspects of the present invention, the washer can be free floating within the compartment. The strap can be affixed to one of the two layers of the base. The stabilizing washer can include tissue in-growth structural material configured in such a way as to form the washer. The stabilizing washer can be coated with a bioabsorbable cross-linked fatty acid based material. The fatty acid based material can be a fish oil. The fatty acid based material can be an omega-3 fatty acid. Likewise, the base can be coated with a bioabsorbable cross-linked fatty acid based material that can be a fish oil and/or an omega-3 fatty acid.

In accordance with further aspects of the present invention, the base can have an outermost perimeter edge comprised of only one of the two layers. The base can be formed of a mesh material suitable for the promotion of tissue in-growth following implantation in a patient.

In accordance with one example embodiment of the present invention, a patch for treating a hernia includes a base having a first layer having a predetermined shape with a central region and an outer perimeter. A second layer of the base has a predetermined shape with a central region and an outer perimeter. A compartment is formed by the placement of the first layer against the second layer and affixation of the first and second layers together. The first and second layers are placed against each other and affixed to each other at affixation points, the affixation points being at locations relatively closer to the outer perimeter of each layer than the central region of each layer in such a way that the central regions of each layer form walls of a compartment therebetween. The first and second layers can be constructed of a structural material suitable for the promotion of tissue in-growth following implantation in a patient. The patch further includes a stabilizing washer disposed within the compartment, and a strap affixed to the base.

BRIEF DESCRIPTION OF THE FIGURES

These and other characteristics of the present invention will be more fully understood by reference to the following detailed description in conjunction with the attached drawings, in which:

FIG. 6A depicts an exploded side view of an exemplary hernia patch 200 inside a patient;

FIG. 6B depicts a side view of an exemplary hernia patch 200, according to one aspect or the present invention;

DETAILED DESCRIPTION

An illustrative embodiment of the present invention relates to a hernia patch that is efficiently implanted, can be readily pulled and maintained against a tissue wall without undue distortion of the patch, and that readily contours and conforms to the tissue wall, eventually promoting tissue in-growth therethrough.

FIGS. 2 through 6B, 7A and 8A, wherein like parts are labeled with like reference numbers throughout, illustrate example embodiments of a hernia patch according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

Exemplary embodiments of the present invention provide a hernia patch that substantially contours and conforms to the abdominal wall and promotes tissue in-growth. In one exemplary embodiment, a hernia patch is provided that includes a base and positioning straps.

Figure 2:
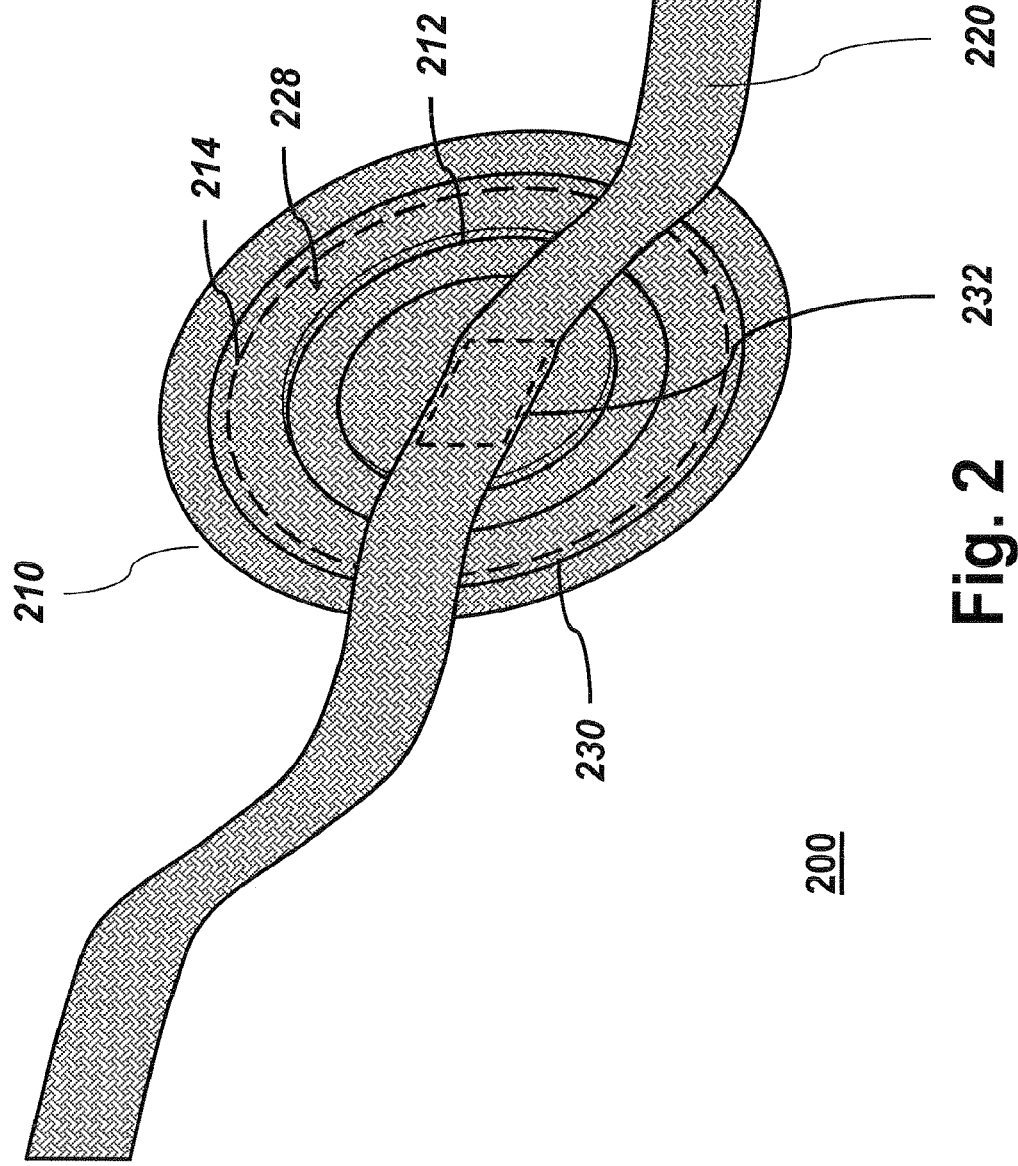
FIG. 2 is a front view of a hernia patch 200 according to an exemplary embodiment of the present invention.

As depicted in FIG. 2, a hernia patch 200 includes a base 210. The base 210 can be formed of two layers, as will be described in more detail below with reference to FIG. 4. A stabilizing washer 212 can be provided between the two layers of the base 210. In accordance with one exemplary embodiment of the present invention, the two layers of the base 210 are affixed to each other at a location 214 between the outer periphery of the stabilizing washer 212 and the outer periphery of the base 210. In further accordance with an exemplary embodiment of the present invention, the stabilizing washer 212 is not affixed to the base, but rather is free-floating. Furthermore, the two layers of the base 210 are not affixed to each other at any location between the inner periphery of the stabilizing washer and the center of the base 210.

The hernia patch 200 can further include a positioning strap 220. The positioning strap 220 is affixed to the top layer of the base, for example using stitching 232. As shown in FIG. 2, the stitching 232 is provided at a central position 223 (see FIG. 4) on the hernia patch 200. In accordance with one exemplary embodiment of the present invention, the positioning strap 220 is affixed only to the top layer of the base 210, and not to both layers of base 210, as described in more detail below with reference to FIG. 4.

Figure 1A:
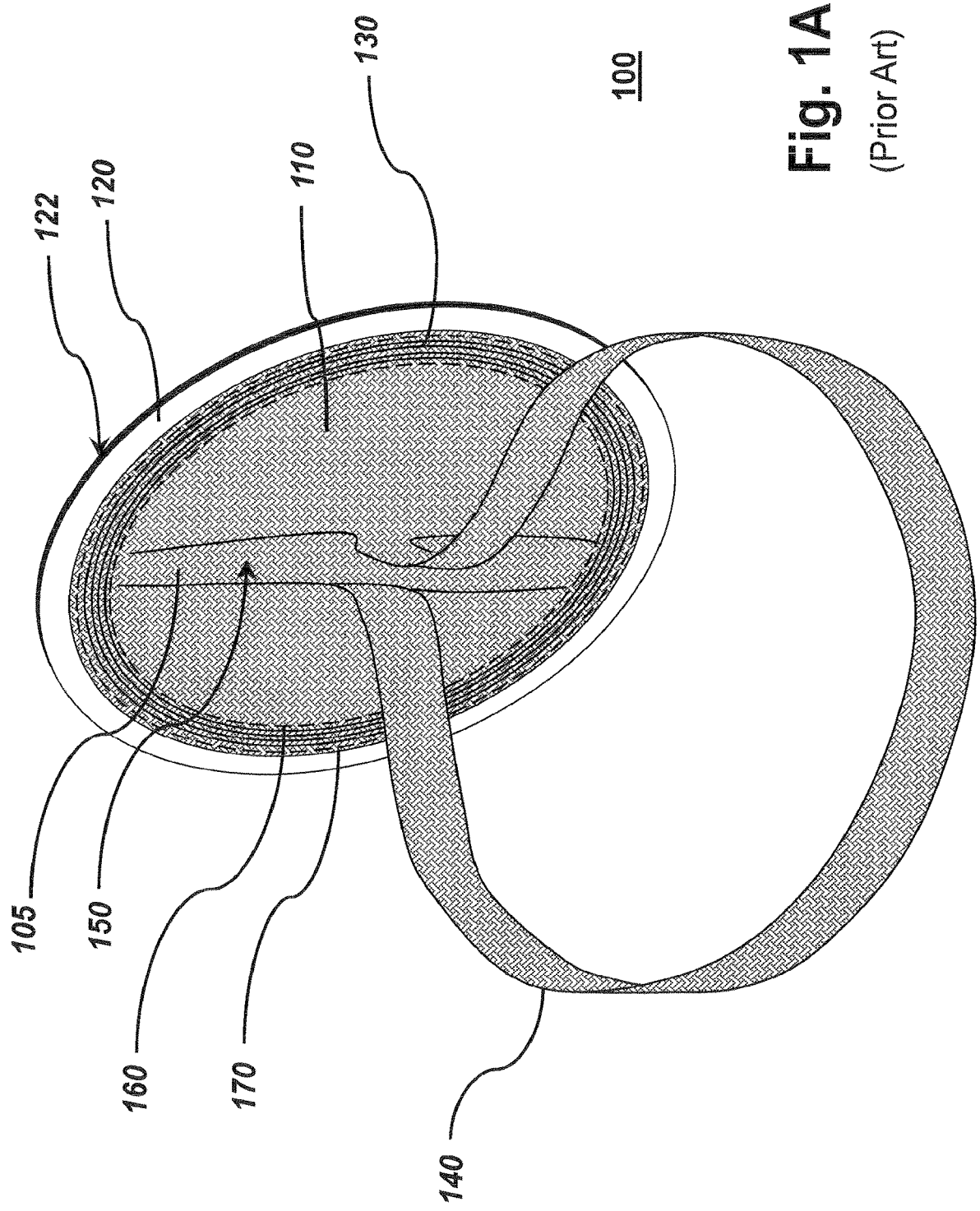
FIG. 1A is a front view of a conventional hernia patch 100.
Figure 1B:
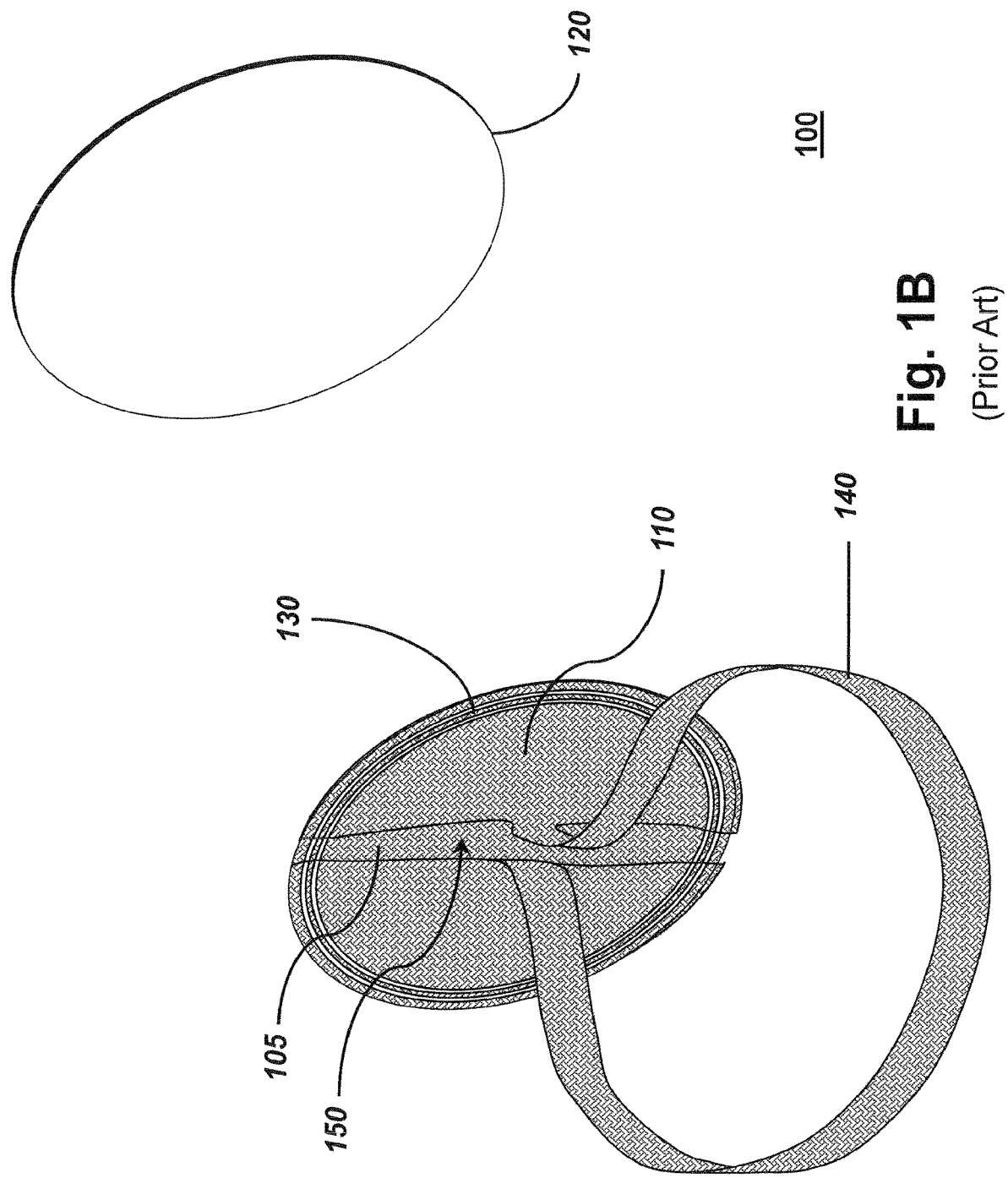
FIG. 1B is an exploded front view of a conventional hernia patch 100.
Figure 3:
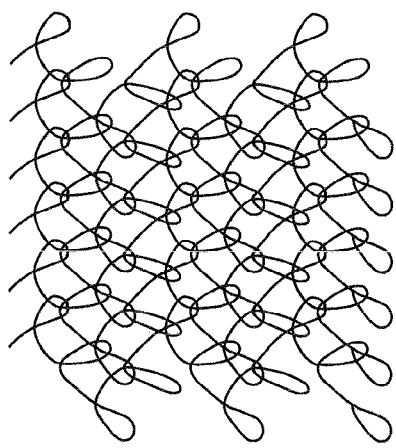
FIG. 3 depicts a mesh material suitable for use in the construction of a positioning strap, the top layer of the base, and the bottom layer of the base in exemplary embodiments of the present invention.

As depicted in FIG. 3, one or more layers of the base and/or the positioning strap may be formed of a mesh 300 material. The mesh 300 may be a semi-permeable structure made of connected strands of flexible or ductile material. As would be understood by one of ordinary skill in the art, the strands of the mesh 300 can be connected using a number of different configurations and methodologies, including but not limited to inter-looping, weaving, braiding, knotting, and the like, as well as being formed directly into a mesh or grid-like pattern. In accordance with one exemplary embodiment of the present invention, the mesh 300 material takes the form of a polypropylene mesh. Examples of polypropylene meshes suitable for use with exemplary embodiments of the invention include, but are not limited to, C-QUR™ Mesh and/or C-QUR Lite™ Mesh, manufactured by Atrium Medical Corporation of Hudson, N.H., and/or can include coated and uncoated mesh materials. Such meshes can be coated with a hydrolysable bioabsorbable cross-linked fatty acid based material, including a partially or fully cured fish oil or omega-3 fatty acid.

Figure 4:
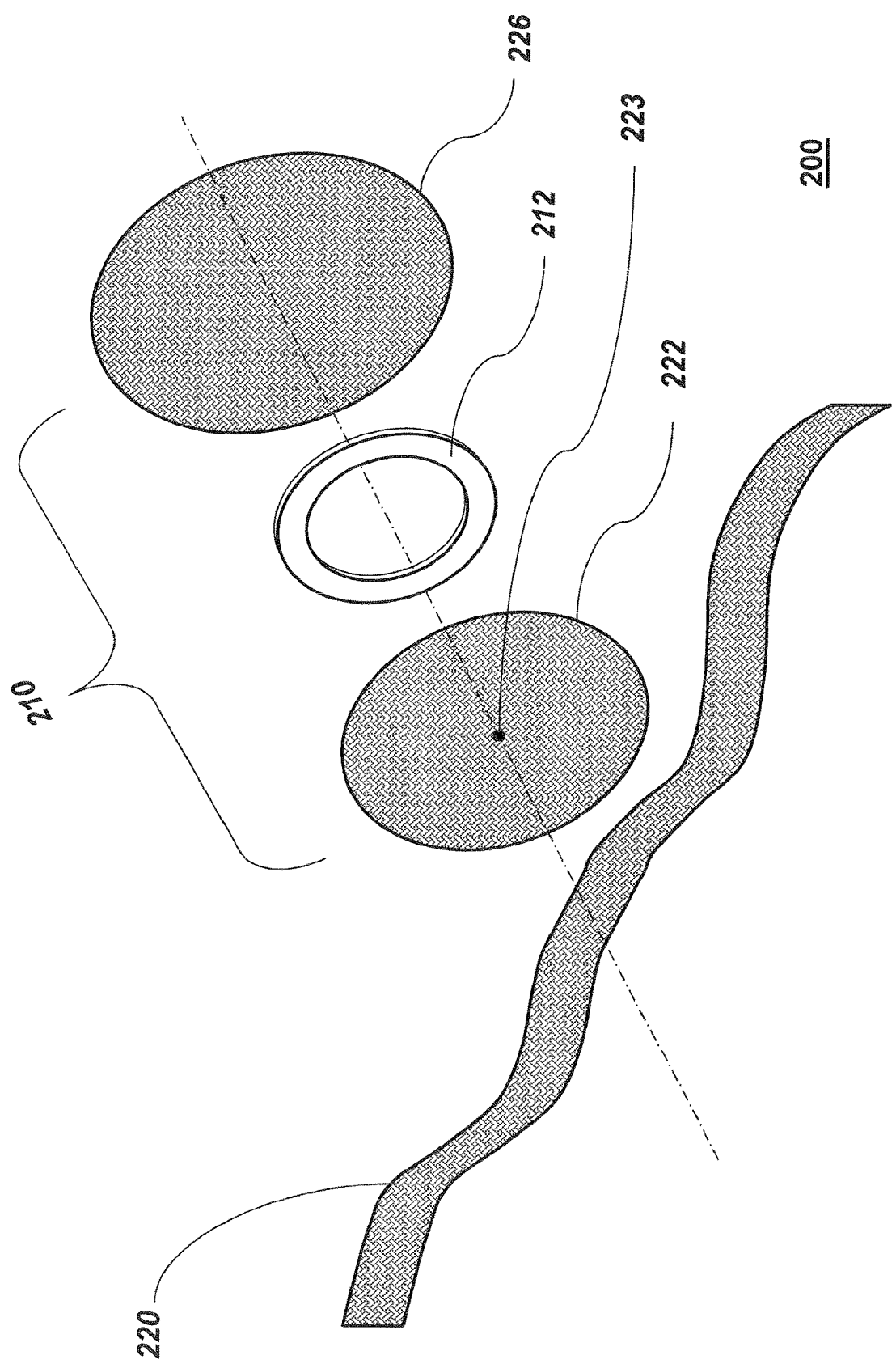
FIG. 4 is an exploded view of a hernia patch 200 according to an exemplary embodiment of the present invention.

FIG. 4 depicts an exploded view of the hernia patch 200 in accordance with embodiments of the present invention. As depicted in FIG. 4, the hernia patch 200 includes the positioning strap 220. The positioning strap 220, as depicted in FIG. 4, is constructed from a mesh 300 material as described herein. One having ordinary skill in the art will recognize that other materials may be suitable for forming the positioning strap 220. In accordance with one exemplary embodiment of the present invention, the positioning strap 220 can be a 1 cm wide length of strap manufactured from a continuous sheet of macro porous C-QUR Lite™ mesh. Each end of the positioning strap 220 may extend approximately ½ cm to either side of the center of the base 210. One having ordinary skill in the art will understand that the dimensions provided herein are exemplary only, and other dimensions may be selected based on the particular application of the hernia patch 200, including the size of the hernia patch 200. Likewise, other dimensional variations, and shape variations, are considered to be within the realm of the capable person of ordinary skill in the art, and therefore included within the scope of the present invention.

The positioning strap 220 is affixed to a top layer 222 of the base 210, for example by stitching the positioning strap 220 to the top layer 222 with a perimeter stitch 230. The positioning strap 220 may be affixed to the top layer 222 by stitching the positioning strap 220 to the top layer 222 at a central position 223. However, one of ordinary skill in the art will appreciate that the positioning strap 220 can be affixed to the base 210 using any number of known fastening technologies that result in a biocompatible configuration, including but not limited to, weaving, braiding, welding, knotting, and the like, in addition to the exemplar stitching described herein.

In accordance with one exemplary embodiment of the present invention, the top layer 222 can be constructed of a mesh 300 material, as described herein, including a polypropylene mesh, such as the above-mentioned C-QUR Lite™ Mesh, or other coated or uncoated mesh materials.

In accordance with one exemplary embodiment of the present invention, the hernia patch 200 further includes a stabilizing washer 212 disposed between the top layer 222 and the bottom layer 226 in a compartment 228 (see FIG. 2) formed therebetween. The compartment 228 is formed by the top layer 222 and the bottom layer 226, as held together by the stitch 230. The stabilizing washer 212 may act as a seal against an abdominal wall when the hernia patch 200 is implanted in a patient. More specifically, the stabilizing washer 212 can act in similar 200 to a skeleton or batten in a sail, providing some additional rigidity to the otherwise very flexible mesh material, such that when the hernia patch 200 is pulled against a tissue surface, the material does not substantially wrinkle, bend, or otherwise give way to the pull force at the point where the force is applied. Rather, the stabilizing washer maintains the hernia patch 200 in a more static position than if the stabilizing washer 212 were not present. The stabilizing washer 212 may be formed from a number of different materials, including but not limited to one or more layers of mesh 300 material. In one exemplary embodiment, the stabilizing washer 212 is formed from three layers of polypropylene mesh, such as ProLite™ Mesh manufactured by Atrium Medical Corporation of Hudson, N.H., configured into the washer shape. One of ordinary skill in the art will further appreciate that the stabilizing washer 212 can be formed in a number of different perimeter shapes (e.g., oval, or other rounded shapes), such that the present invention is by no means limited to a flat circular washer shape.

The stabilizing washer 212 may further be coated, for example, with a cured hydrolysable bioabsorbable cross-linked fatty-acid based material. The fatty acid-based material may comprise an oil that may be natural, such as a fish oil. Alternatively, the fatty acid-based material may be derived from synthetic sources. The fatty acid-based material can comprise a biological oil, such as an oil containing at least one lipid or omega-3 fatty acid, including a fish oil. The biomaterial can include vitamin E.

The fatty acid-based material may be cured, for example by heat curing. Alternatively, the fatty acid-based material may be cured using oil autoxidation or photo-oxidation chemistry, or any other suitable curing method known in the art.

The top layer 222 of the hernia patch 200 is affixed to the bottom layer 226. For example, the top layer 222 may be stitched to the bottom layer 226 of the hernia patch 200. The top layer 222 may be affixed to the bottom layer 226 at a location peripheral to the stabilizing washer 212 (see, e.g., FIG. 2).

In one exemplary embodiment, the bottom layer 226 is constructed of a coated polypropylene mesh, such as the above-mentioned C-QUR™ Mesh, whose physical properties and characteristics are understood by those of ordinary skill in the art. Such a mesh includes a hydrolysable bioabsorbable cross-linked fatty acid based material, including a partially or fully cured fish oil or omega-3 fatty acid. Such a coating can be applied with sufficient thickness to serve as a physical protective layer between surrounding tissue and the surface of the mesh structure. Such a protective layer, when constructed in such a manner, can provide protection upon initial implantation against abrasions when surrounding tissue is pressed or rubbed against the protective layer and mesh. The coating flattens out or smoothes out the surface of the mesh, to reduce or eliminate the potential for abrading nearby tissue. Over time, the bioabsorbable coating is slowly absorbed by the surrounding tissue and fluids, and tissue in-growth is allowed to penetrate through the mesh, in the place of the bioabsorbable coating. As such, the underlying mesh structure is eventually engulfed by tissue in-growth, which again flattens or smoothes out the mesh structure relative to nearby tissue, eliminating the potential for abrasions. Such a coated mesh structure (e.g., C-QUR™ Mesh) differs substantially from the prior art provision of an ePTFE layer that does not allow tissue in-growth therethrough, and can wrinkle, warp, or the like at implantation, or over time, creating tissue separation and gaps (see, e.g., FIGS. 7B and 8B). The use of a hydrolysable bioabsorbable coating on the mesh as described herein enables better incorporation of the implant over time into the tissue in such a way as to cause the least amount of disruption and complications following implantation. Likewise, to the extent such a hydrolysable bioabsorbable coating is incorporated into the stabilizing washer 212, after implantation, over time, the coating is absorbed and there is tissue in-growth into the washer 212, thus maintaining a stabilizing ability while being incorporated and engulfed by the tissue.

Figure 5B:
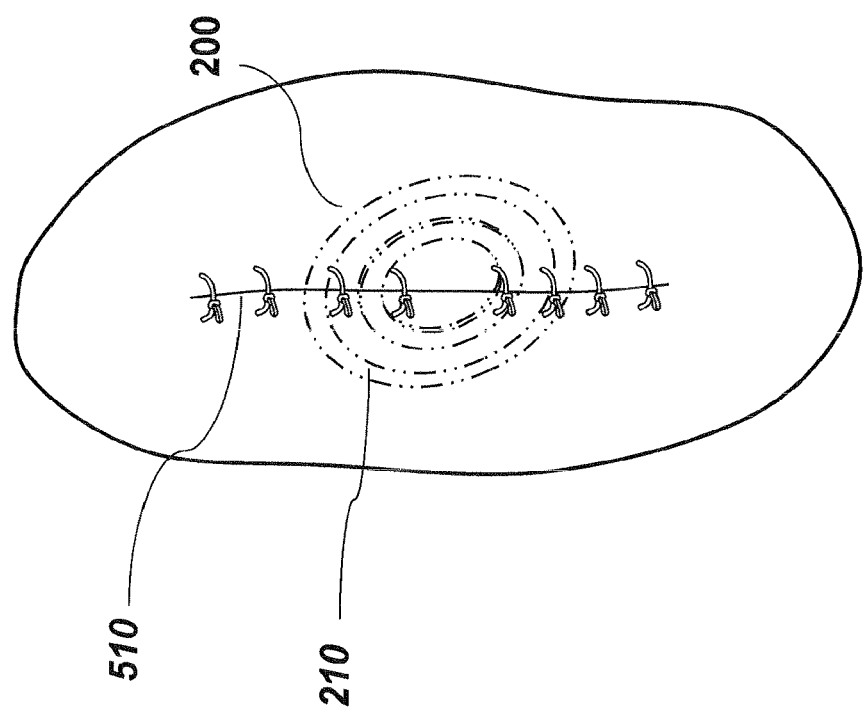
FIG. 5B depicts the exemplary hernia patch 200 of FIG. 5A after deployment inside a patient.
Figure 5A:
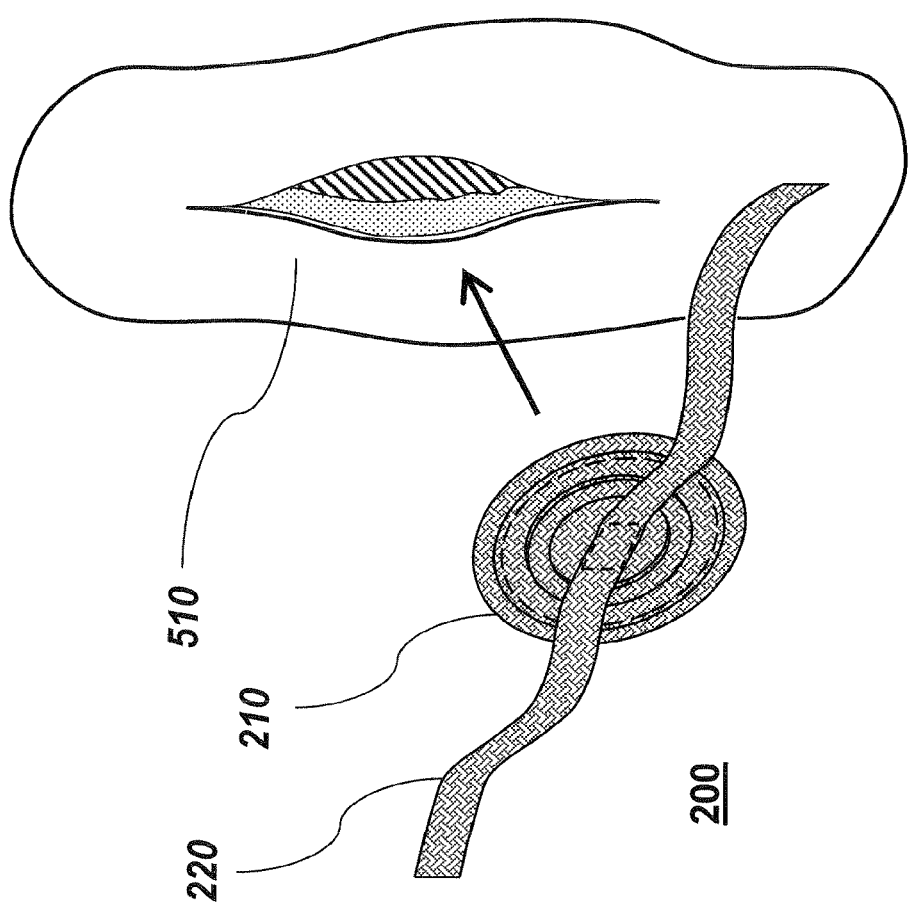
FIG. 5A depicts an exemplary hernia patch 200 being deployed according to an exemplary embodiment of the present invention.

FIG. 5A and FIG. 5B depict the hernia patch 200 as utilized in the repair of a hernia. As shown in FIG. 5A, an incision 510 is made near a hernia defect. The base 210 of the hernia patch 200 is inserted into the incision 510. During the insertion process, the shape of the base 210 may be elastically deformed (e.g., folded in half) so that the base 210 fits inside the incision. The stabilizing washer 212 is sufficiently elastic or flexible to be able to be folded in half for the insertion and then return back to its original shape or configuration once inside the incision. The act of folding the stabilizing washer 212 in half does not cause plastic deformation of the stabilizing washer 212 if constructed in accordance with the preferred embodiment of the present invention. A clinical user may maneuver the hernia patch into position and pull the hernia patch tightly up against the abdominal wall using the positioning strap 220.

As shown in FIG. 5B, once the hernia patch is inserted into the incision, the base 210 opens back into its original planar configuration due to the degree of elasticity, flexibility, or stiffness of the stabilizing washer 212. Some of the positioning strap 220 remains after a substantial portion is trimmed off. As would be well understood by those of ordinary skill in the art, the small remaining portion of the positioning strap 220 may be sutured to the edge of the hernia defect, or alternatively the clinical user may suture the top layer 222 of the base 210 of the hernia patch to the abdominal wall (not shown in this figure). The suturing most often occurs prior to the trimming of the strap 220. The skin is then closed over the hernia defect and the patch, as depicted in FIG. 5B.

FIG. 6A depicts an exploded side view of the hernia patch 200 in use. Specifically, FIG. 6A depicts the base 210 of the hernia patch 200, and the positioning strap is not shown in FIG. 6A for clarity. The top layer 222 of the hernia patch 200 is located adjacent to tissue 620 of a patient, such as, e.g., an abdominal wall. Due to the structure of the hernia patch 200, including its elastic properties and ability to flex with minimal forces (such as those resulting from pressing the hernia patch 200 against the tissue) the hernia patch 200 is free to conform to the shape of the abdominal wall tissue 620. By conforming to the shape of the abdominal wall tissue, what is meant is that the surface of the hernia patch 200 facing the tissue has the ability to bend and flex to follow the contours of the tissue, such that there are no substantial spaces or gaps formed between the hernia patch 200 and the tissue, due to the hernia patch 200 being too rigid or stiff (such as with the prior conventional hernia patch 100 described previously herein). The stabilizing washer 212 and the bottom layer 226 are also depicted.

FIG. 6B depicts a side view the hernia patch 200 in use. The positioning strap is not shown in FIG. 6B for clarity. As shown in FIG. 6B, the top layer 222 of the hernia patch 200 has been sutured using sutures 650 to the site of the incision. The top layer 222 is stitched to the bottom layer 226 at a location 214 between the outer periphery of the stabilizing washer 212 and the outer periphery of the base 210. As further shown in FIG. 6B, the top layer 222 and the bottom layer 226 are sized and dimensioned such that an outer periphery 670 of the base includes only a single layer of mesh. By having only a single layer of mesh (e.g., the top layer 222 or the bottom layer 226), the ability of the perimeter edge of the hernia patch 200 to flex and conform to the tissue is improved versus if the perimeter were to include multiple layers of material, or more rigid material.

The exemplary embodiments of the hernia patch 200 described herein offer several advantages over the conventional hernia patch. Because of the structure and position of the positioning strap, the positioning strap spans the hernia defect even when tension is placed on the straps. This allows the hernia patch to be positioned more accurately and with less deformation when the hernia patch is being deployed. In addition, the positioning strap described above allows the exemplary hernia patch to be positioned without the need for a pocket, as in the conventional hernia patch. Accordingly, in exemplary embodiments depicted herein, no pocket is provided.

The exemplary embodiments described above include a particular structure formed as a result of the structure of the stabilizing washer and the stitching that affixes the top layer of the base to the bottom layer of the base. Because the stabilizing washer is free floating, and the top layer and the bottom layer of the base are affixed to each other peripheral to the stabilizing washer, the body of the hernia patch contours to the abdominal wall when tension is placed on the positioning straps.

In addition, the stabilizing washer has a sufficient stiffness to unfold the base of the hernia patch after insertion, yet likewise has sufficient flexibility to fold and insert into the defect without cracking or permanently deforming the washer. Further, the single layer of mesh provided around the perimeter of the hernia patch allows the hernia patch to conform to irregularities in the tissue, including tissue such as the abdominal wall, peritoneum, and pre-peritoneal fat. Because the hernia patch can conform to these irregularities, any spaces or gaps between the patch and the patient's body are sealed off. Accordingly, viscera does not become trapped in these spaces or gaps and the odds of a surgical adhesion or hernia recurrence are reduced.

An inventive hernia patch 200 according to an exemplary embodiment as described herein was tested in the same preclinical swine study as the conventional patch 100 as described herein. As was done for the conventional hernia patch 100, the inventive hernia patch 200 was explanted at 28 days after laparoscopic images of the hernia patch were taken at days 1, 7, 14, and 28 post implantation. The results showed that, unlike the conventional hernia patch, the inventive hernia patch was tightly apposed to the abdominal wall after 24 hours in-vivo.

Figure 7B:
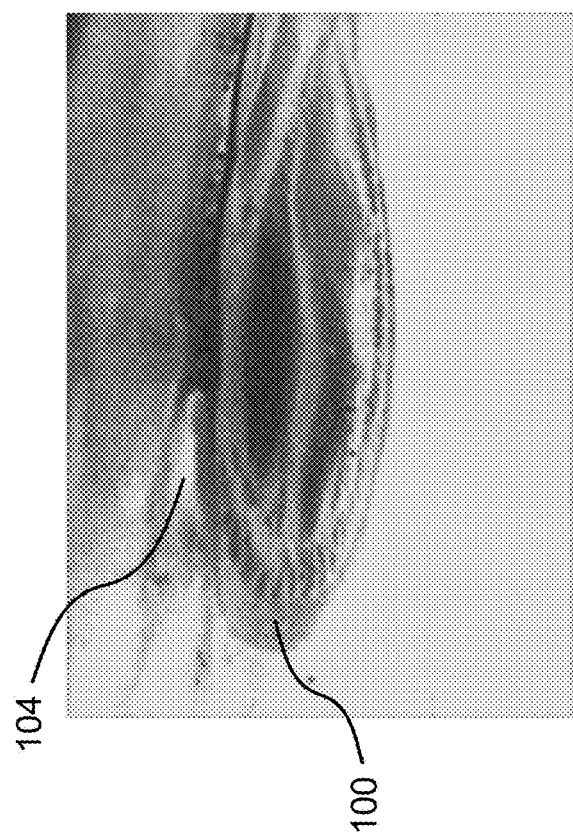
FIG. 7B is an image of a conventional hernia patch 100, 24 hours after implantation.
Figure 7A:
FIG. 7A is an image of a hernia patch 200 in accordance with the present invention, 24 hours after implantation.
Figure 8B:
FIG. 8B is a cross-sectional image of the conventional hernia patch 100 of FIG. 7B, after explant at 28 days post-implantation.
Figure 8A:
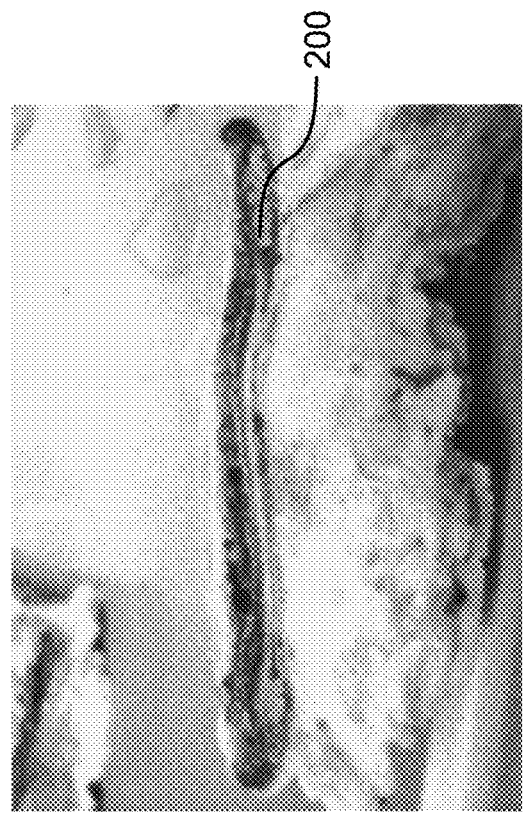
FIG. 8A is a cross-sectional image of the inventive hernia patch 200 of FIG. 7A, after explant at 28 days post-implantation.

As shown in FIG. 7A, the inventive hernia patch 200 substantially contours and conforms with the tissue, especially around its perimeter edge 202. In addition, after 28 days, both the top layer and the bottom layer of the inventive hernia patch were completely infiltrated with tissue and incorporated into the abdominal wall, as can be seen in FIG. 8A. Whereas the conventional hernia patch 100 did not conform well to the shape of the tissue, as shown in FIG. 7B. Instead the conventional hernia patch 100 formed wrinkles and allowed spaces 104 to form around the perimeter of the conventional hernia patch 100, similar in fashion to a potato chip. After 28 days, the conventional hernia patch 100 did not support any tissue in-growth around the perimeter, as is evident in the explant image shown in FIG. 8B. The lack of tissue in-growth is expected, due to the existence of the densified polypropylene bonded to a layer of ePTFE 120. Such materials are not expected to promote tissue in-growth. In contrast, the inventive hernia patch 200 effectively reduced these spaces and conformed to the shape of the abdominal wall. After 28 days, as is evident in the explant image shown in FIG. 8A, the tissue in-growth through the hernia patch 200 is extensive, and virtually eliminates any spacing between the hernia patch 200 and the tissue of the abdominal wall. Furthermore, the inventive hernia patch 200 includes use of the positioning straps in such a way that the hernia patch 200 does not invert on the perimeter or edge during placement.

Although the present invention has been described with respect to exemplary embodiments, one having ordinary skill in the art will understand that the present invention is not limited to the exemplary embodiments described herein.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A patch for treating a hernia, comprising:
   a base consisting of two adjacent, mesh layers and a tissue conformable stabilizing washer disposed within a continuous interior compartment between the two adjacent, mesh layers, the continuous interior compartment extending continuously from an outer periphery of the stabilizing washer to a center of the base, wherein the two adjacent, mesh layers are affixed to each other only at a location between the outer periphery of the stabilizing washer and an outer periphery of the base in such a way as to form the continuous interior compartment with the stabilizing washer free floating therein, wherein the two adjacent, mesh layers are not affixed to each other at any location between an inner periphery of the stabilizing washer and the center of the base; and
   a positioning strap attached to the base in such a way that when a pull force is applied thereto, the base is pulled by the positioning strap toward a tissue location, and the base is configured to conform against the tissue location.

2. The patch of claim 1, wherein the base configured to conform against the tissue location comprises a surface that is configured to face the tissue location and bend and flex to follow contours of the tissue in such a way that there are no spaces or gaps formed between the base and the tissue after implantation.

3. The patch of claim 1, wherein the positioning strap is affixed to only one of the two adjacent, mesh layers of the base.

4. The patch of claim 1, wherein the stabilizing washer comprises tissue in-growth structural material configured in such a way as to form the stabilizing washer.

5. The patch of claim 1, wherein the base is formed of a mesh material suitable for the promotion of tissue in-growth following implantation in a patient.

6. The patch of claim 1, wherein the base has an outermost perimeter edge comprised of only one of the two layers.

7. A patch for treating a hernia, comprising:
   a base consisting of two adjacent, mesh layers and a tissue conformable stabilizing washer disposed within a continuous interior compartment between the two adjacent, mesh layers, the continuous interior compartment extending continuously from an outer periphery of the stabilizing washer to a center of the base, wherein the two adjacent, mesh layers are affixed to each other only at a location between the outer periphery of the stabilizing washer and an outer periphery of the base in such a way as to form the continuous interior compartment with the stabilizing washer free floating therein, wherein the two adjacent, mesh layers are not affixed to each other at any location between an inner periphery of the stabilizing washer and the center of the base, and wherein the stabilizing washer is coated with a bioabsorbable cross-linked fatty acid based material; and
   a positioning strap attached to the base in such a way that when a pull force is applied thereto, the base is pulled by the positioning strap toward a tissue location, and the base is configured to conform against the tissue location.

8. The patch of claim 7, wherein the fatty acid based material comprises a fish oil.

9. The patch of claim 7, wherein the fatty acid based material comprises an omega-3 fatty acid.

10. A patch for treating a hernia, comprising:
    a base consisting of two adjacent, mesh layers and a tissue conformable stabilizing washer disposed within a continuous interior compartment between the two adjacent, mesh layers, the continuous interior compartment extending continuously from an outer periphery of the stabilizing washer to a center of the base, wherein the two adjacent, mesh layers are affixed to each other only at a location between the outer periphery of the stabilizing washer and an outer periphery of the base in such a way as to form the continuous interior compartment with the stabilizing washer free floating therein, wherein the two adjacent, mesh layers are not affixed to each other at any location between an inner periphery of the stabilizing washer and the center of the base, and wherein the base is coated with a bioabsorbable cross-linked fatty acid based material; and
    a positioning strap attached to the base in such a way that when a pull force is applied thereto, the base is pulled by the positioning strap toward a tissue location, and the base is configured to conform against the tissue location.

11. The patch of claim 10, wherein the fatty acid based material comprises a fish oil.

12. The patch of claim 10, wherein the fatty acid based material comprises an omega-3 fatty acid.

* * * * *